United States Patent
Clemente

(10) Patent No.: US 9,308,121 B2
(45) Date of Patent: Apr. 12, 2016

(54) HELICAL AIR DISTRIBUTION SYSTEM

(76) Inventor: Roger Clemente, Hazlet, NJ (US)

(*) Notice: Subject to any disclaimer, the term of this patent is extended or adjusted under 35 U.S.C. 154(b) by 984 days.

(21) Appl. No.: 13/374,865

(22) Filed: Jan. 20, 2012

(65) Prior Publication Data

US 2012/0203311 A1  Aug. 9, 2012

Related U.S. Application Data

(60) Provisional application No. 61/462,646, filed on Feb. 7, 2011.

(51) Int. Cl.
*A61F 7/00* (2006.01)
*B60H 1/00* (2006.01)
*F24D 5/00* (2006.01)
*A61F 7/02* (2006.01)

(52) U.S. Cl.
CPC .............. *A61F 7/00* (2013.01); *A61F 2007/006* (2013.01); *A61F 2007/0067* (2013.01); *A61F 2007/0228* (2013.01); *B60H 1/00264* (2013.01); *F24D 5/00* (2013.01); *Y10T 137/85938* (2015.04)

(58) Field of Classification Search
CPC ..... F28D 7/04; A61F 2007/0228; A61F 7/00; B60H 1/00264
USPC .............. 607/107–112; 62/259.3; 2/436, 437, 2/DIG. 1
See application file for complete search history.

(56) References Cited

U.S. PATENT DOCUMENTS

| | | | | |
|---|---|---|---|---|
| 2,955,432 A * | 10/1960 | Hardebol et al. | ................... | 62/5 |
| 3,495,385 A * | 2/1970 | Glass | .............................. | 96/306 |
| 4,276,874 A * | 7/1981 | Wolvek et al. | .................. | 600/18 |
| 4,284,133 A * | 8/1981 | Gianni et al. | .................. | 165/133 |
| 5,303,425 A * | 4/1994 | Mele | ................................. | 2/115 |
| 5,533,354 A * | 7/1996 | Pirkle | ......................... | 62/259.3 |
| 5,588,968 A * | 12/1996 | Sternlicht | ...................... | 607/107 |
| 6,009,564 A * | 1/2000 | Tackles et al. | .................... | 2/436 |
| 6,688,128 B1 * | 2/2004 | Robbie et al. | ................. | 62/259.3 |
| 6,814,733 B2 * | 11/2004 | Schwartz et al. | ............... | 606/41 |
| 7,628,801 B2 * | 12/2009 | Westlund et al. | .............. | 607/112 |
| 7,716,940 B2 * | 5/2010 | Farnworth et al. | ............ | 62/259.3 |
| 8,366,720 B2 * | 2/2013 | Mitelberg et al. | ............. | 606/108 |
| 2008/0097462 A1 * | 4/2008 | Mitelberg et al. | ............. | 606/108 |
| 2008/0145285 A1 * | 6/2008 | Olbert et al. | .................. | 422/220 |
| 2008/0231795 A1 * | 9/2008 | Cartier | ............................. | 351/49 |
| 2009/0242042 A1 * | 10/2009 | Cardona et al. | ............... | 137/486 |
| 2010/0025009 A1 * | 2/2010 | Klett et al. | ....................... | 165/46 |
| 2010/0293993 A1 * | 11/2010 | Rini et al. | ........................ | 62/507 |
| 2010/0319381 A1 * | 12/2010 | Hubler et al. | ................. | 62/259.3 |
| 2012/0137414 A1 * | 6/2012 | Saylor | ............................... | 2/435 |

* cited by examiner

*Primary Examiner* — Kaitlyn Smith
*Assistant Examiner* — Yasamin Ekrami
(74) *Attorney, Agent, or Firm* — Clifford G. Frayne

(57) ABSTRACT

A self-contained helical air distribution system for the body of an individual which can distribute air over both the chest and back of the individual, the system including a battery operated blower fan in communication with the plenum and manifold, the manifold having a plurality of tubular distribution conduits, each conduit having a capped end, the conduits extending over the chest and back of the body, the conduits formed with a spiral helix cut allowing the tubular conduits to react to the motion of the human body, the spiral helix cuts reacting to such movement, thereby allowing air to selectively escape from the expansion of these cuts providing a cooling and evaporate effect. With slight adaptation the air distribution system can distribute heated air and also be used to control the ambient temperature about inanimate objects, such as computers, electronic instruments, windshields, and car seats.

8 Claims, 8 Drawing Sheets

US 9,308,121 B2

HELICAL AIR DISTRIBUTION SYSTEM

RELATED APPLICATIONS

Applicant claims the benefit of provisional application Ser. No. 61/462,646, filed Feb. 7, 2011.

BACKGROUND OF THE INVENTION

1. Field of the Invention

The present invention relates to a helical air distribution system for particular use by an individual who is required to wear restrictive, heavy protective clothing and/or equipment in an ambient atmosphere conducive to excessive perspiration, the system including a self-contained fan and tubular distribution system for distribution of air over the body of the individual. While the present invention is described and has a particular cooling and evaporative effect to humans, it can also have application to animals, such as race horses, as well as with respect to the movement of heat from one body to another by means of radiation, convection and conduction from inanimate objects, such as computers, electronic equipment, or the like, which must maintain a similar preferred operating temperature.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights.

2. Description of the Prior Art

Individuals are oftentimes required to perform physical activity or duty in ambient atmosphere which is conducive to perspiration. Construction workers in hot climates oftentimes find themselves in such situations, however, they are not always required to wear heavy equipment, and the situation is such that they can take frequent rest breaks, seek out shaded areas, and hydrate when needed.

Other individuals performing in such ambient temperatures are not often allowed the luxury of rest breaks and the like. These include military personnel, which are often required to wear tactical protective vests and multiple layers of clothing, in addition to the personal military equipment they must carry with them. Similar workers are those involved in hazardous waste clean up, which they have to wear protective gloves, boots, and outer clothing, together with protective headgear and face masks. These individuals are subjected to substantial fluid loss due to the clothing they are wearing, the equipment they are carrying, and the ambient thermal atmosphere.

Therefore there has been a need for a self-contained apparatus which can be worn by an individual in such conditions which is light weight, comfortable, and distributes air flow about the body of the individual, including the chest and the back. Such a system needs to be responsive of the body and not be subject to shut down or collapse by the movement of the body. That is, the individual should be able to lie on his stomach, lie on his back, or sit with his back against a rigid object without the system shutting down or ceasing the distribution and flow of air about the body.

Cooling garments have been widely explored and include systems which attempt to blot the moisture and perspiration from the body, as well as incorporation an air flow system which is incorporated within a protective vest to distribute air yet such a system compromises the performance of the protective vest.

There are numerous personal cooling systems to prevent heat overload and stress. The advantages, methods and construction have been well documented. Currently, vest or garment systems that keep the body cool use phase change material, air, compressed gas, ice, water or a circulating refrigerated liquid. U.S. Pat. No. 6,257,011 B1 to Siman-Tov, et al. teaches an air moving channel sheet capable of absorbing evaporative liquid. U.S. Pat. No. 6,874,332 B2 to Forgach teaches a vest having a fan to discharge air through its elongated housing. U.S. Pat. No. 5,533,354 to Pirkle teaches a harness constructed of perforated tubing which uses a gas to circulate air over the body.

None of the above have a stand alone pressurized movable flexible discharge outlet air system that is capable of channeling the exhausting air in a multi-directional, circular swirling pattern as it exits the helical, spiraled sections of conduit adjacent the body's surface area.

Applicant's system is a lightweight tubular system which distributes a flow of air about the body, the flow of air itself cooling the body and also serving as an evaporative stream for the evaporation of moisture and perspiration. Further, with slight adaptation the apparatus may distribute heated air.

OBJECTS OF THE INVENTION

An object of the present invention is to provide for a self-contained air transfer system which can be worn by an individual adjacent the body, the system distributing air about the body.

A further object of the present invention is to provide for a novel flexible air transfer system which is lightweight and which is easily worn beneath the clothing and equipment of the individual.

A still further object of the present invention is to provide for a novel flexible air transfer system which is responsive to the movement of the body.

A still further object of the present invention is to provide for a novel flexible air transfer system which allows the individual to perform normal bodily movement, such as sitting, lying prone, lying supine, without affecting the integrity of the system or interrupting the flow of air.

A still further object of the present invention is to provide for a novel flexible air transfer apparatus which distributes air flow over the body of an individual or animal, the distributed air flow providing a cooling and evaporative effect.

A still further object of the present invention is to provide for a novel flexible air transfer apparatus which with slight adaptation can distribute heated air about the body of an individual or animal.

A still further object of the present invention is to provide for a novel self-contained helical air distribution system which can be independently worn with or without clothing, the discharge system distributing air about the desired portion of the body of a human or animal.

A still further object of the present invention is to provide for a novel flexible air transfer system which is responsive to the movement of the body of the individual or animal.

A still further object of the present invention is to provide for a novel air transfer apparatus for animate or inanimate objects to maintain a desired temperature level.

SUMMARY OF THE INVENTION

A self-contained helical air distribution system for the body of an individual which can distribute air over both the chest and back of the individual, the system including a battery operated blower fan in communication with the plenum and manifold, the manifold having a plurality of tubular distribution conduits, each conduit having a capped end, the conduits extending over the chest and back of the body, the conduits formed with a spiral helix cut allowing the tubular conduits to react to the motion of the human body, the spiral helix cuts reacting to such movement by opening and closing, thereby allowing air to selectively escape from the expansion of these cuts providing a cooling and evaporate effect. With slight adaptation the air distribution system can distribute heated air and also be used to control the ambient temperature about inanimate objects, such as computers, electronic instruments, windshields, and car seats.

BRIEF DESCRIPTION OF THE DRAWINGS

These and other objects of the present invention will become apparent, particularly when taken in light of the following illustrations wherein.

DETAILED DESCRIPTION OF THE INVENTION

Figure 1:
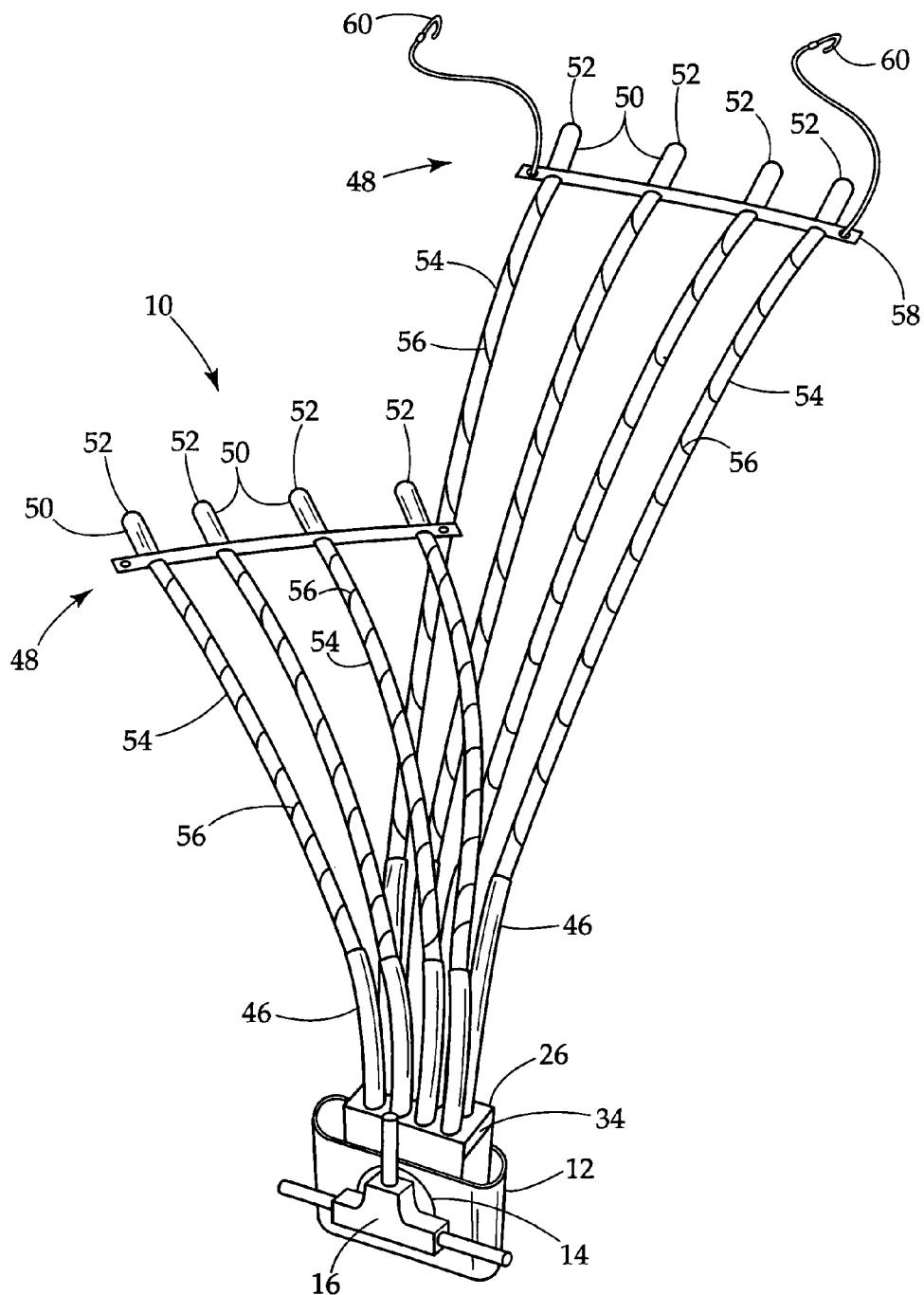
FIG. 1 is a front view of the self-contained helical air distribution system of the present invention.
Figure 2:
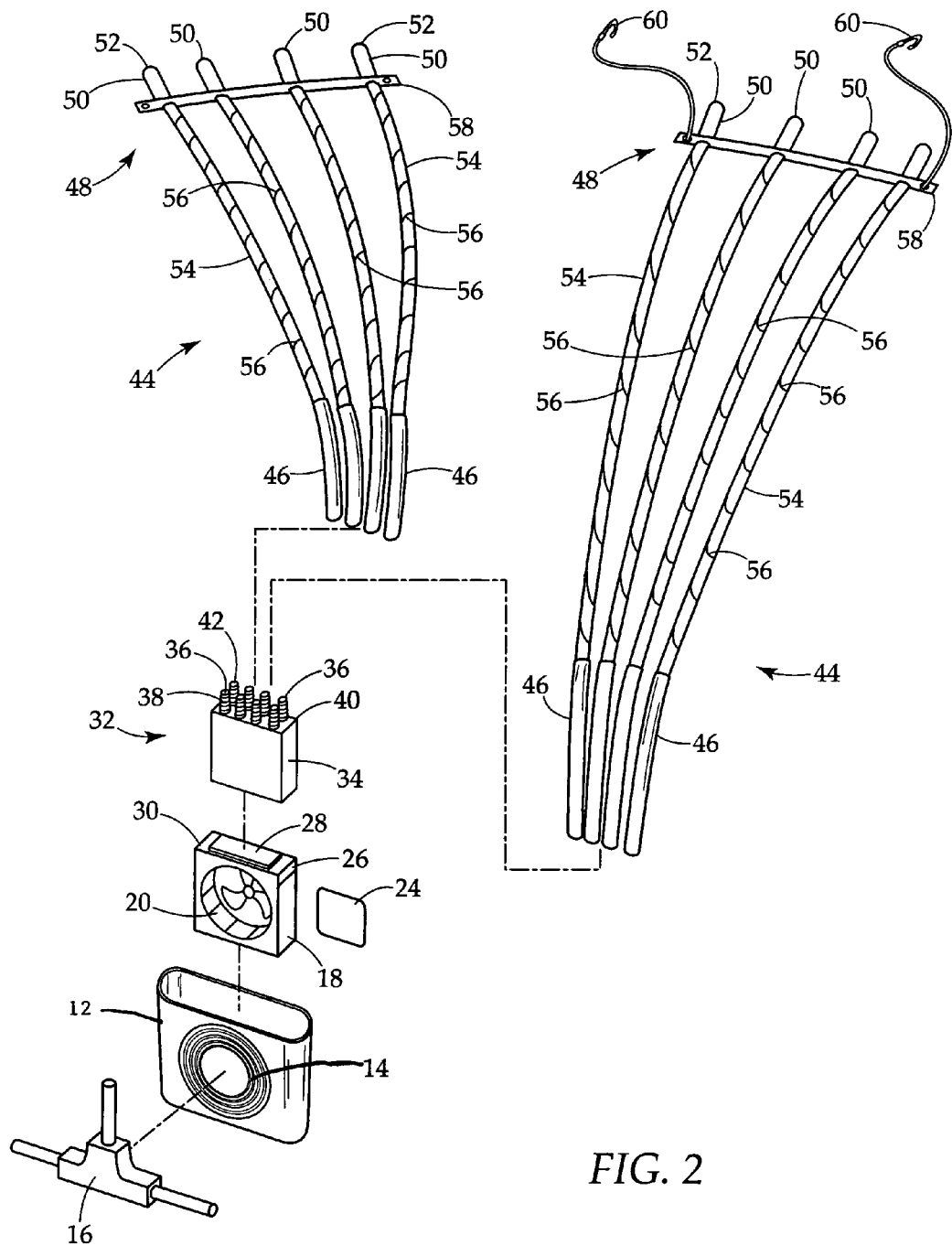
FIG. 2 is an exploded view of the helical self-contained air distribution system of the present invention.

FIG. 1 is a front view of the self-contained helical air distribution system of the present invention and FIG. 2 is an exploded view. The self-contained helical air distribution system 10 is described initially with respect to its adaption to use by a human individual who is required to perform physical activity in ambient atmosphere which is conducive to excessive perspiration. This would include construction workers, astronauts, military personnel, and hazardous waste clean up individuals and others who oftentimes are required to wear substantial protective clothing and equipment. The distribution of air by the system will have a cooling and evaporative effect on the individual wearing the system. It will be understood as later described, that the self-contained helical air distribution system can also have application to animals, and particularly animals which compete in events which contribute to perspiration, such as racehorses, as well as to inanimate objects, and in particular, delicate inanimate objects, such as computers, servers and the like, which are oftentimes required to perform in excessive ambient thermal conditions, such as on a military vehicle.

The self-contained helical air distribution system 10 as illustrated in FIGS. 1 and 2 is adapted for human use. The system comprises an outer protective shell 12 to shield the contents from dirt, dust, and particulate matter. The outer protective shell 12 is formed with an optional filter aperture 14 in alignment with and in communication with an inlet ductwork 16 removably affixed to the outer protective shell 12. Positioned within the outer protective shell is an electric blower fan assembly 18 that is energized by a battery pack 24 or other power supply that is connected to a selective on/off switch 26. The electric blower fan assembly 18 is slidably receivable within the outer protective shell 12 such that it is in alignment with the optional filter aperture 14, the electric blower fan assembly 18 having an inlet port 20 and an outlet port 28 on its upper surface 30.

Outlet port 28 has secured thereto an outlet manifold 32 comprising a plenum chamber 34, and a plurality of extending nozzles 36. The plurality of extending nozzles 36 illustrated in FIGS. 1 and 2 are upstanding, but it will be recognized by one of ordinary skill in the art that their orientation may vary without departing from the scope of the invention. The upstanding nozzles 36 are preferably formed of decreasing concentric ridges 38 decreasing in circumference from their base 40 to the upper orifice 42 for frictional engagement with distribution conduits as described hereafter.

Secured to extending nozzles 36 are a plurality of tubular distribution conduits 44. In the embodiment illustrated in FIGS. 1 and 2, each of these distribution conduits 44 is formed with a resilient flexible solid lower tubular member 46 each of which is frictionally engageable with a selective extending nozzle 36. The opposing end 48 of each of these tubular distribution conduits 44 is capped with a resilient flexible tubular member 50 having a closed end 52. Secured within and between resilient flexible tubular members 46 and 50 is a resilient flexible tubular conduit 54 having a helical, spiral-like slot gap 56 formed upon its longitudinal length. This resilient flexible tubular conduit 54 having a helical, spiral-like slot along its longitudinal length is designed to respond to body movement, thus causing the slot gap 56 to expand and contract with body movement and open and close randomly along its length as more fully disclosed hereafter.

The upper terminus of the tubular distributive conduits 44 proximate their cap ends are secured by resilient flexible harness members 58. These harness members 58 are removably securable to each other by means of a resilient flexible fastener or fasteners 60 which can be secured to the ends of the harness members. Tubular distribution conduits 44 have been described as flexible for the particular use as illustrated in the following drawings. However there may be some instances where the tubular distribution members 44 may be rigid or semi-rigid to obtain the desired results.

Figure 3:
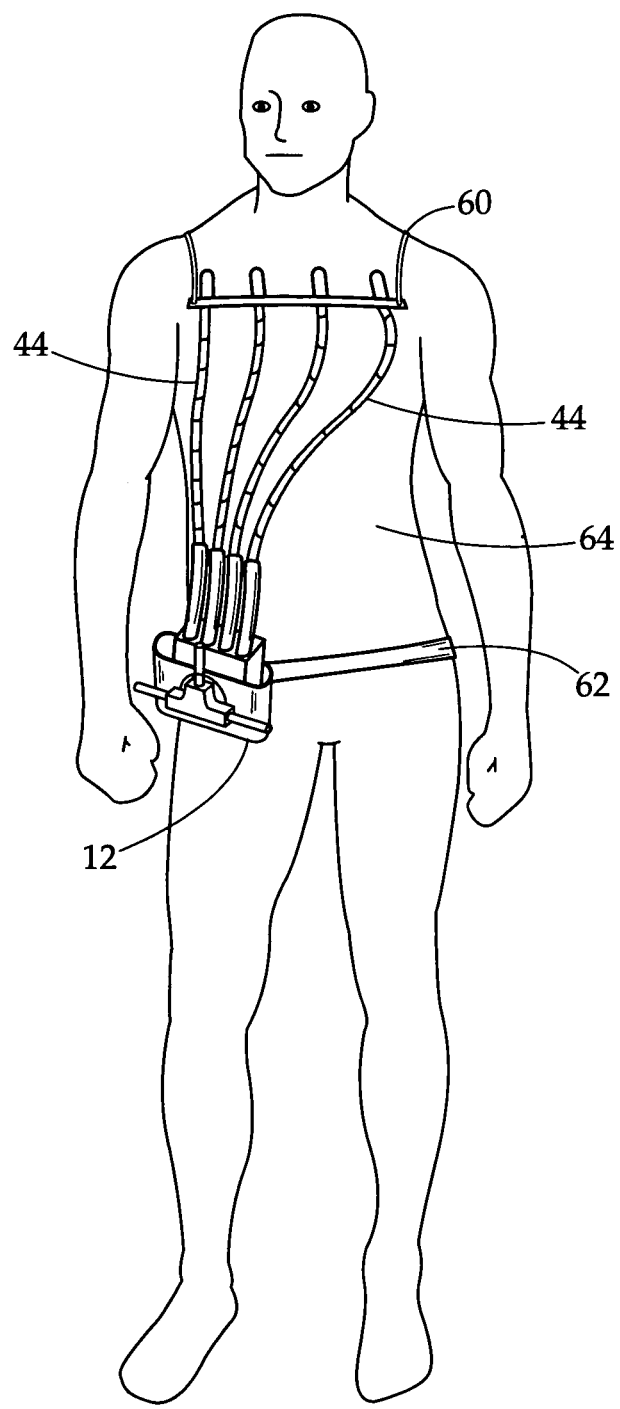
FIG. 3 is a front view of the self-contained helical air distribution system positioned about the torso of an individual.
Figure 4:
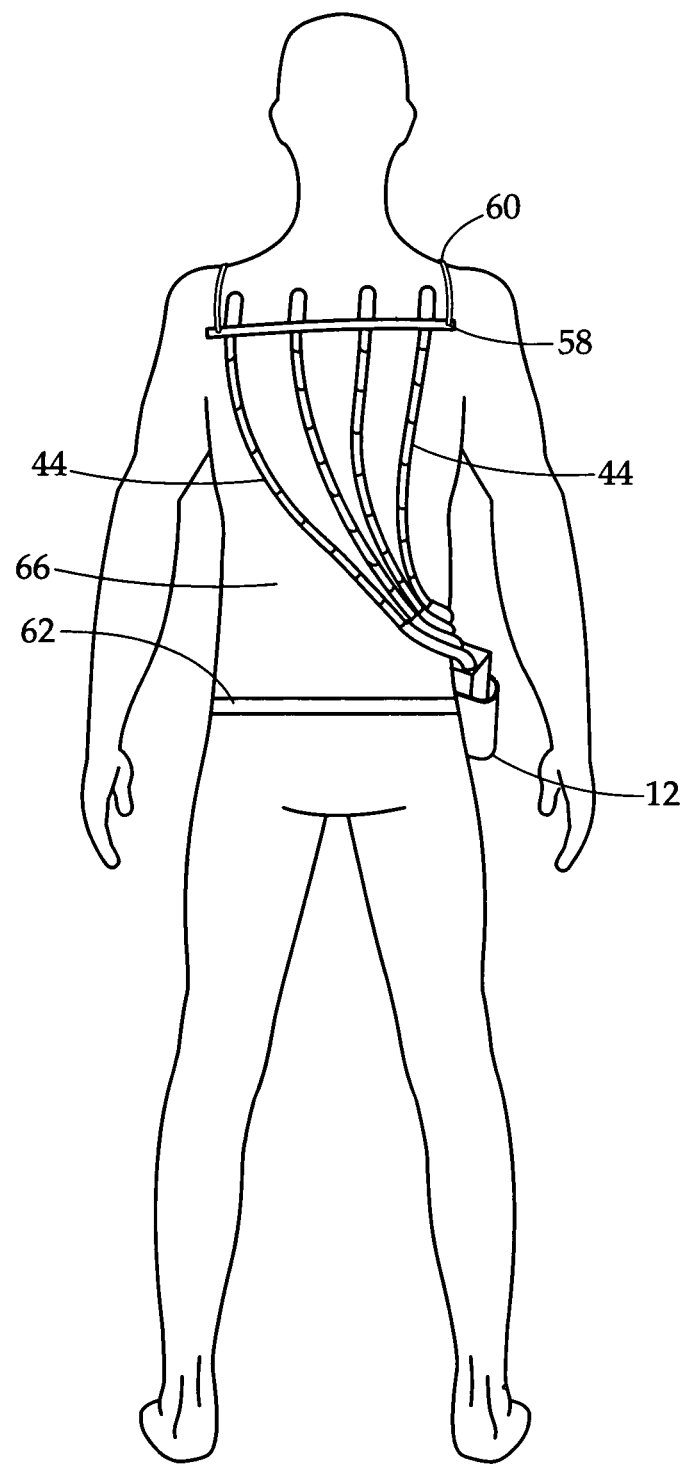
FIG. 4 is a rear view of the self-contained helical air distribution system disposed about the torso of an individual.

FIG. 3 is a front view of the self-contained helical air distribution system 10 of the present invention worn on an individual, and FIG. 4 is a rear view. The outer protective shell 12 of the device would include a securing means in the form of a belt clip or the like which would allow the self-contained helical air distribution system to be worn on the waist of an individual secured by a belt 62. In the preferred embodiment a first set of tubular distribution conduits 44 would extend upwardly from the extended nozzles 36 over the front torso 64 of the individual. A second set of tubular distributive conduits 44 would extend upwardly about the waist of the individual and cover and distribute air to the rear portion 66 of the individual's torso. The resilient flexible harness members 58 would be secured by the resilient flexible securing fastener 60 over the shoulders 68 of the individual.

The self-contained helical distribution system once positioned as illustrated in FIGS. 3 and 4 would respond to the movement of the individual in that the slot gap 56 in the resilient flexible tubular distribution conduits 44 would open and close in response to the movement of the upper torso of the individual's body. This allows the individual to assume a prone, supine, sitting, leaning, or kneeling position and still allow air circulation to occur over the front and rear portion of the torso.

The self-contained helical distribution system being light weight does not present a significant load to the individual with respect to other equipment or garments which he may be carrying or wearing. The protective garments, equipment, or clothing required by the individual would be worn over the self-contained distributive evaporating system.

In the embodiment illustrated, there are eight extended nozzles illustrated extending upwardly from the plenum chamber. In this embodiment, four aligned nozzles are associated with four distribution conduits which cover the individual's front torso and four aligned nozzles and their associated distribution conduits are associated with the coverage of the rear torso. It has been found that four such conduits provide adequate and possibly optimum coverage of the torso for evaporative cooling in the conditions anticipated. However, it should be noted that fewer or more distributive conduits may be utilized without departing from the spirit and scope of the invention, and may be required depending upon the extreme thermal conditions which are being encountered. Upon operation the electric blower fan assembly 18 intakes ambient air through inlet port 20 and discharges it through outlet port 28 pressurizing plentium chamber 34 and distributing conduits 44. The pressurized air then travels through flexible tubular conduits 54 exiting the helical cut openings 56. As the air passes over the torso 64 it evaporates body sweat, cooling the body. The optimal operation of the system, the distribution conduits 44 would be distributed about the torso and adjacent the torso of the individual. However the system will provide the same affect, although not as optimally, if there is clothing between the conduits and the torso of the individual.

Figure 5:
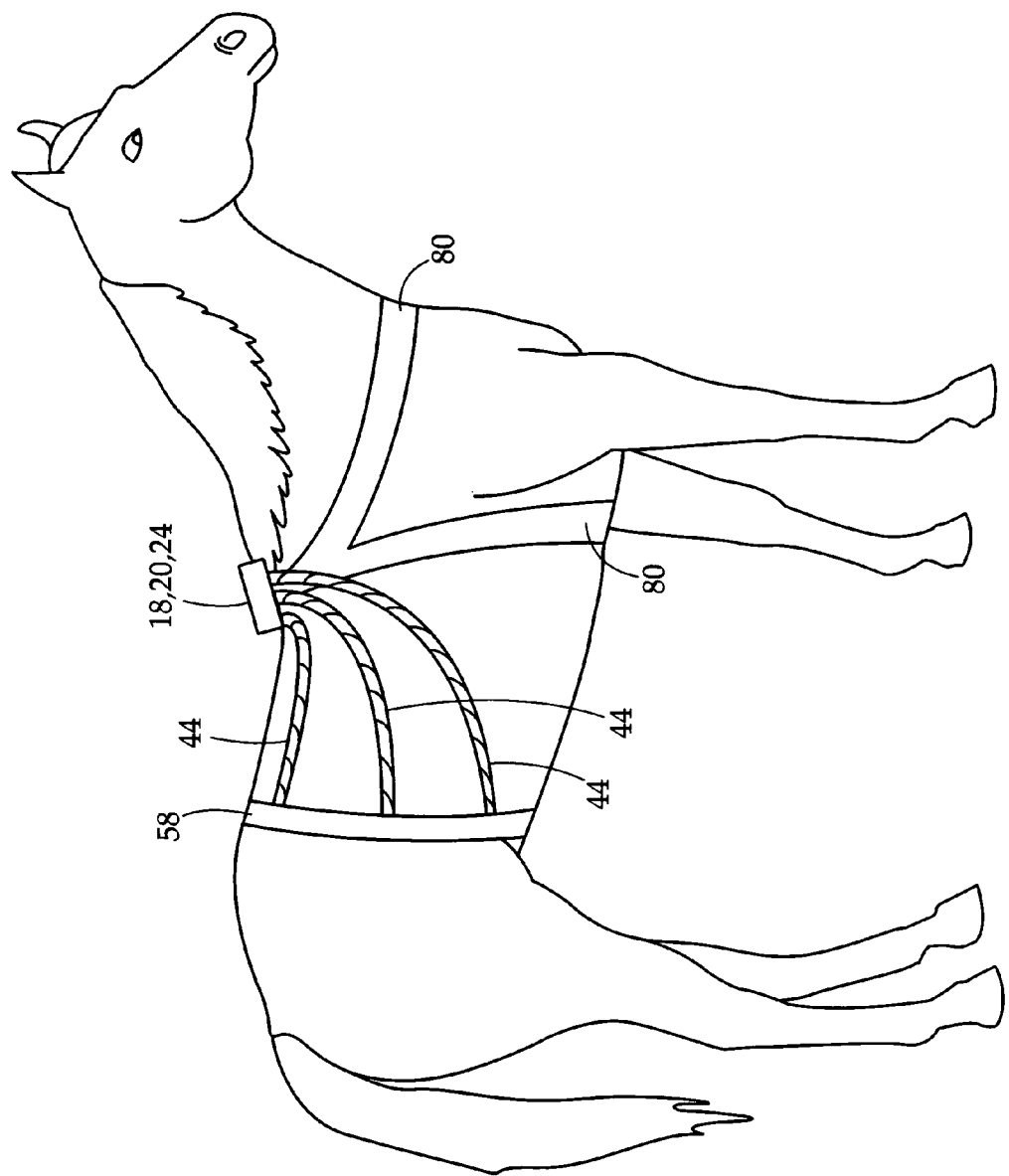
FIG. 5 is a side view of the self-contained helical air distribution system disposed about the body of a horse.

FIG. 5 is a side view of the helical aid distribution system 10 of the present invention as applied to an animal which undertakes vigorous exercise, such as a race horse, or similarly situated animal. In this instance, system structure is identical to that previously described, but the system is secured to the animal by a harness 80. Naturally, if the animal such as a horse, which is considerably larger than a human, the electric blower fan assembly 18, plentium chamber 32, and distributive conduits 44 may be larger than that associated with a human being. Similarly, with a smaller animal the system would be secured by a harness, but the electric blower fan assembly and the distributive conduits may be smaller and of a shorter length.

Figure 6:
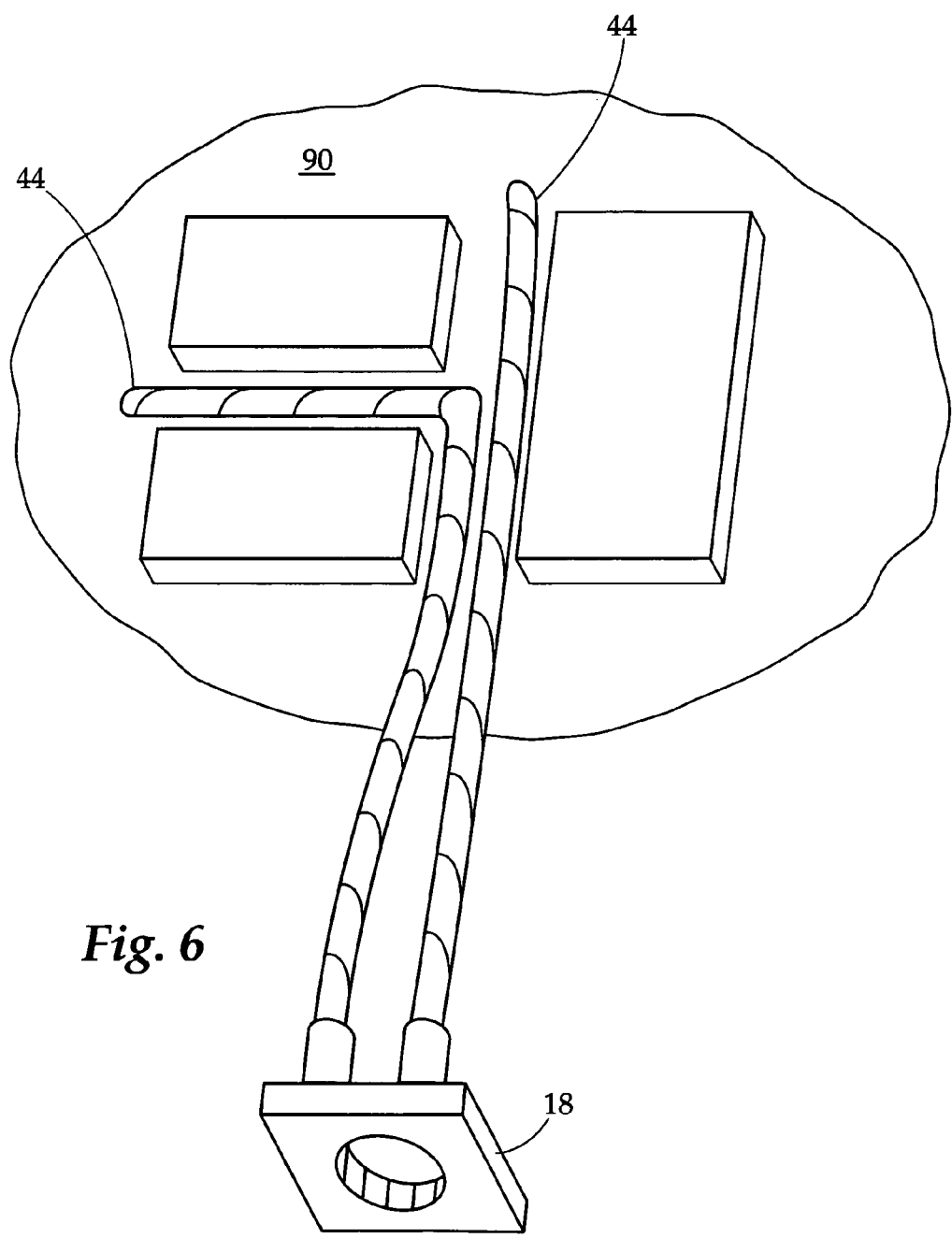
FIG. 6 is a perspective view of the helical air distribution system disposed within a computer server.

FIG. 6 illustrates the use of the helical air distribution cooling system as applied to an inanimate object 90, a portion of a computer circuit board, server, or cabinet. With the wide spread use of digital and computer technology, many computers, computer servers and the like find themselves installed or operating in the situations of extreme thermal ambient atmospheres. In many military vehicles, systems are controlled and operated by onboard computers and these vehicles may operate in extreme weather conditions. There therefore is a need to maintain the proper temperature of the computer in these conditions and to insure that particulate matter in the form of dirt, dust and the like, does not penetrate or invade the internals of the system.

Applicant's helical air distribution system lends itself to such a cooling and filtering purpose due to the distribution conduits 44, being resilient and flexible, and can be directed and wound in very circuitous patterns within the device or cabinet so as to allow cooling air to escape from the slot gaps 56 in the distributive conduits 54 in appropriate locations within the device or cabinet to maintain the proper temperature. In such a system, mounted on a vehicle, the power source for the motor and fan module may come directly from the vehicle as opposed to battery packs as envisioned for use by humans and animals. Still further, in such a system, the electric blower fan assembly may be larger than that envisioned for a human or an animal, since it will be transported by the vehicle and not by an individual, and thus weight concerns are less of a factor.

Figure 7:
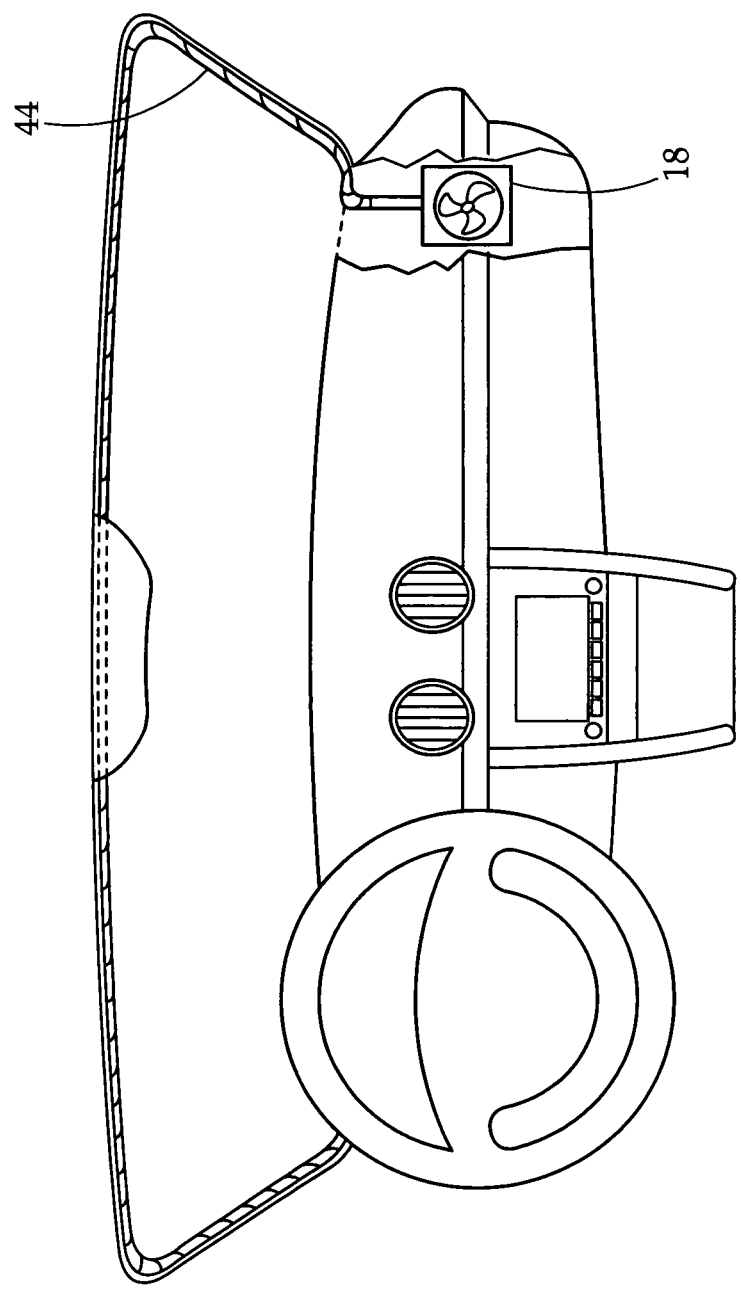
FIG. 7 is a front view of the helical air distribution system disposed about a windshield.
Figure 8:
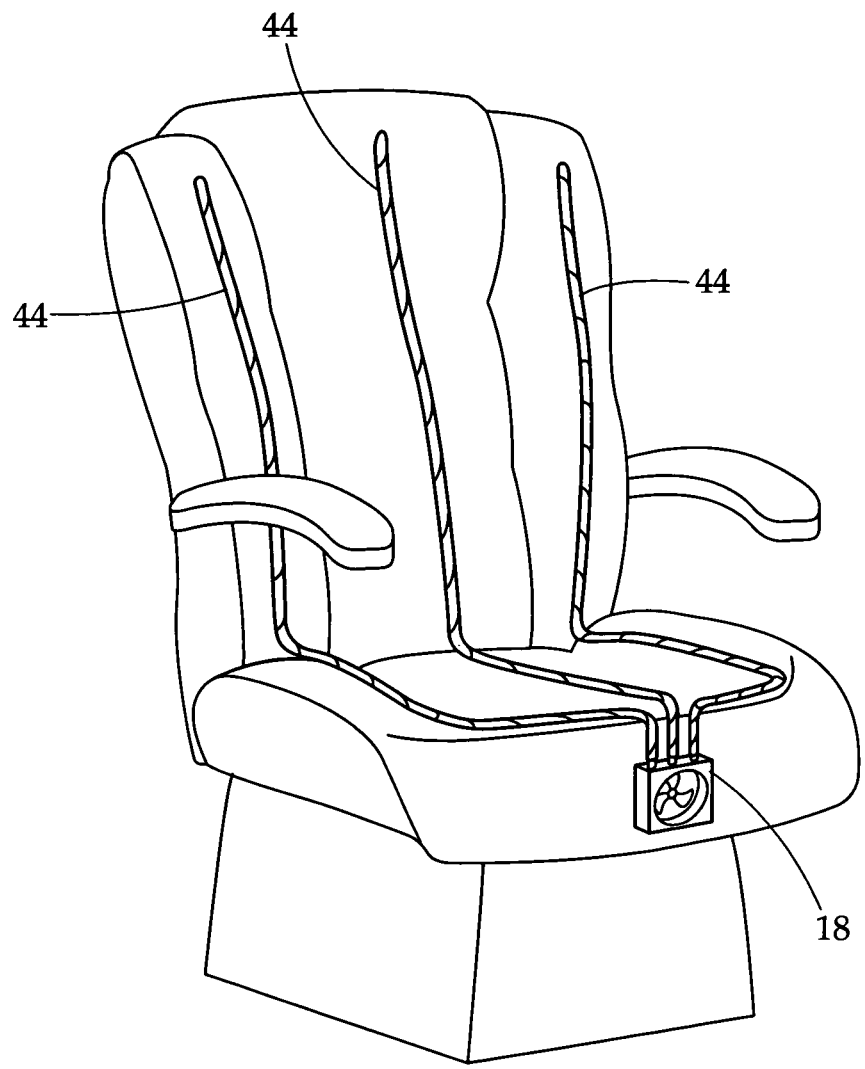
FIG. 8 is a front view of the helical air distribution system of the present invention disposed within a car seat.

FIGS. 7 and 8 illustrate the air distribution system of the present invention with respect to other inanimate objects to which it may have application. FIG. 7 illustrates the tubular distribution conduits disposed about the windshield of a vehicle providing direct air flow through the slot gaps 56 to the windshield to prevent fogging and to accomplish defogging or defrosting of the windshield. FIG. 8 illustrates the disposition of the tubular distribution conduits 44 about the seat of a vehicle in order to provide a cooling effect to the seat of the vehicle, and the comfort of the individual in the seat, particularly if the individual were required to maintain a sitting orientation for a length of time.

While the present air distribution system has been described with respect to a cooling and evaporative effect for animate objects and a cooling effect for inanimate objects, it will be recognized by those skilled in the art that the addition of a battery powered resistance element prior to the intake or incorporated into the plenum of the device, could be utilized to preheat the air before distribution by means of the tubular conduits 54 and slot gaps 56 to provide a heating effect to the individual, animal, or inanimate object.

Therefore, while the present invention has been disclosed with respect to the preferred embodiments thereof, it will be recognized by those of ordinary skill in the art that various changes and modifications can be made without departing from the spirit and scope of the invention. It is therefore manifestly intended that the invention be limited only by the claims and the equivalence thereof.

I claim:

1. A helical air distribution system for controlling an ambient temperature immediately adjacent an animate object, the helical air distribution system comprising:
    a power source for a blower fan, said blower fan in communication with a plenum chamber and a manifold, said manifold having a plurality of flexible tubular distribution conduits extending there from, each flexible tubular distribution conduit having a capped extended end, each conduit having formed therein a spiral helix slit, said spiral helix slit configured to open and close along the length of said flexible tubular distribution conduit in response to the motion and movement of an animate object and configured to distribute air through said spiral helix slits.

2. The helical air distribution system in accordance with claim 1 wherein said blower fan, said plenum chamber, and said manifold are secured to a belt member, said plurality of flexible tubular distribution conduits being secured to a first harness member and a second harness member, said first harness member and said second harness member secured by flexible securing harness, said first harness member and said second harness member and said flexible tubular distribution conduits positioned under an apparel of clothing.

3. The helical air distribution system in accordance with claim 2 wherein said distribution of air promotes the evaporation of perspiration and the cooling of an animate object.

4. The helical air distribution system in accordance with claim 3 wherein a heating member is incorporated with said manifold to heat said air prior to distribution through said flexible tubular distribution conduits.

5. The helical air distribution system in accordance with claim 1 wherein said flexible air distribution conduits are resilient and semi-rigid.

6. The helical air distribution system in accordance with claim 1 is a portable self-contained system.

7. The helical air distribution system in accordance with claim 1 wherein said system is functional and operational when worn either outside or beneath an apparel of clothing.

8. The helical air distribution assembly in accordance with claim 1 wherein said flexible tubular distribution conduits and said spiral helical slit are configured to respond to body movement, permitting said spiral helical slits to open and close.

* * * * *